(12) United States Patent
Su et al.

(10) Patent No.: US 10,513,734 B2
(45) Date of Patent: *Dec. 24, 2019

(54) INTEGRATED PHOTONIC ELECTRONIC SENSOR ARRAYS FOR NUCLEIC ACID SEQUENCING

(71) Applicant: Intel Corporation, Santa Clara, CA (US)

(72) Inventors: Xing Su, Cupertino, CA (US); Mark Oldham, Emerald Hills, CA (US)

(73) Assignee: Intel Corporation, Santa Clara, CA (US)

( * ) Notice: Subject to any disclaimer, the term of this patent is extended or adjusted under 35 U.S.C. 154(b) by 340 days.

This patent is subject to a terminal disclaimer.

(21) Appl. No.: 15/457,244

(22) Filed: Mar. 13, 2017

(65) Prior Publication Data

US 2017/0183727 A1    Jun. 29, 2017

Related U.S. Application Data

(63) Continuation of application No. 14/142,603, filed on Dec. 27, 2013, now Pat. No. 9,593,371.

(51) Int. Cl.
| | |
|---|---|
| *C12Q 1/68* | (2018.01) |
| *C12Q 1/6874* | (2018.01) |
| *C12Q 1/6869* | (2018.01) |
| *G01N 27/00* | (2006.01) |
| *G01N 27/414* | (2006.01) |

(52) U.S. Cl.
CPC ......... *C12Q 1/6874* (2013.01); *C12Q 1/6869* (2013.01); *G01N 27/00* (2013.01); *G01N 27/4145* (2013.01)

(58) Field of Classification Search
None
See application file for complete search history.

(56) References Cited

U.S. PATENT DOCUMENTS

| | | |
|---|---|---|
| 7,888,013 B2 | 2/2011 | Miyahara |
| 7,923,240 B2 | 4/2011 | Su |
| 8,500,979 B2 | 8/2013 | Elibol |
| 8,741,117 B2 | 6/2014 | Daniels |

(Continued)

FOREIGN PATENT DOCUMENTS

| | | |
|---|---|---|
| WO | 2009-149125 | 12/2009 |
| WO | 2012162429 | 11/2012 |

(Continued)

OTHER PUBLICATIONS

Punj et al. (A plasmonic 'antenna-in-box' platform for enhanced single-molecule analysis at micromolar concentrations, Nature Nanotechnology 8, 512-516 (2013), Published online Jun. 9, 2013).*

(Continued)

*Primary Examiner* — Aaron A Priest
(74) *Attorney, Agent, or Firm* — Trop, Pruner & Hu, P.C.

(57) ABSTRACT

Devices and methods for detecting, identifying, and sequencing, compounds, complexes, and molecules are described. Electronic detection is combined with optical excitation to determine the presence or identity of an analyte of interest. Embodiments of the invention additionally provide devices and methods that allow highly parallel nucleic acid sequence determination.

18 Claims, 9 Drawing Sheets

(56) References Cited

U.S. PATENT DOCUMENTS

| | | | |
|---|---|---|---|
| 2002/0177695 A1* | 11/2002 | Grinstaff | C07H 19/06 536/23.1 |
| 2003/0143556 A1* | 7/2003 | Blackburn | B82Y 15/00 506/4 |
| 2003/0143581 A1* | 7/2003 | Franzen | B82Y 5/00 435/6.11 |
| 2005/0215031 A1 | 9/2005 | Ouchi | |
| 2006/0199193 A1 | 9/2006 | Koo | |
| 2009/0032401 A1 | 2/2009 | Ronaghi | |
| 2009/0087850 A1 | 4/2009 | Eid | |
| 2009/0140128 A1 | 6/2009 | Oldham | |
| 2009/0170716 A1 | 7/2009 | Su | |
| 2009/0247418 A1 | 10/2009 | Castro | |
| 2009/0305909 A1 | 12/2009 | Nordman et al. | |
| 2010/0300899 A1 | 12/2010 | Levine | |
| 2011/0065588 A1 | 3/2011 | Su | |
| 2011/0170103 A1 | 7/2011 | Gomez-Rivas | |
| 2011/0250402 A1* | 10/2011 | Oldham | G01N 21/648 428/172 |
| 2011/0306039 A1 | 12/2011 | Chiou | |
| 2011/0319276 A1 | 12/2011 | Liu | |
| 2012/0046176 A1* | 2/2012 | Su | C12Q 1/6874 506/2 |
| 2012/0091365 A1* | 4/2012 | Moerner | G01N 21/64 250/459.1 |
| 2012/0220471 A1 | 8/2012 | Gomez Rivas et al. | |
| 2013/0109577 A1 | 5/2013 | Korlach | |
| 2013/0281325 A1 | 10/2013 | Elibol | |
| 2014/0001055 A1 | 1/2014 | Elibol | |
| 2014/0001341 A1 | 1/2014 | Hassibi | |
| 2014/0083866 A1 | 3/2014 | Daniels | |
| 2014/0178862 A1 | 6/2014 | Su | |
| 2014/0190824 A1 | 7/2014 | Credo | |
| 2014/0299485 A1 | 10/2014 | Daniels | |
| 2015/0065353 A1 | 3/2015 | Turner | |
| 2015/0080232 A1* | 3/2015 | Ju | C12Q 1/6827 506/4 |

FOREIGN PATENT DOCUMENTS

| | | | | |
|---|---|---|---|---|
| WO | 2012-162429 | 5/2014 | | |
| WO | 2015-074001 | 5/2015 | | |
| WO | 2015074004 | 5/2015 | | |
| WO | WO-2015074004 A1 * | 5/2015 | | C12Q 1/6869 |

OTHER PUBLICATIONS

Kinkhabwala et al. (Large single-molecule fluorescence enhancements produced by a bowtie nanoantenna, Nature Photonics 3, 654-657 (2009), Published online: Oct. 18, 2009).*

Vrabel et al. (Base-modified DNA labeled by [Ru(bpy)(3)](2+) and [Os(bpy)(3)](2+) complexes: construction by polymerase incorporation of modified nucleoside triphosphates, electrochemical and luminescent properties, and applications, Chemistry. 2009; 15(5):1144-54, Dec. 15, 2008).*

Anderson (Intel, PacBio Researchers Among Team Taking on Exploratory Project Pairing SMRT Sequencing with Electronic Tags, available at https://www.genomeweb.com/sequencing/Intel-pacbio-researchers-among-team-taking-exploratory-project-pairing-smrt-sequ, Oct. 29, 2012).*

Niedringhaus et al., "Landscape of Next-Generation Sequencing Technologies," American Chemical Society, Anal. Chem. 2011,83, pp. 4327-4341.

Eid et al., "Real-Time DNA Sequencing from Single Polymerase Molecules," Science vol. 323, Jan. 2, 2009, pp. 133-138.

Fuller et al., "The challenges of sequencing by synthesis," Nature Biotechnology, vol. 27, No. 11, Nov. 6, 2009, 11 pages.

Gupta et al., "The effect of the 3',5' thiophosphoryl linkage on the exonuclease activities of T4 polymerase and the Klenow fragment," Nucleic Acids Research, vol. 12, No. 14, Jul. 25, 1984, 15 pages.

Knorre et al., "General method for the synthesis of ATP gamma-derivatives," FEBS Letters, vol. 70, No. 1, Nov. 1976, pp. 105-108.

Korlach et al., "Long, Processive Enzymatic DNA Synthesis Using 100% Dye-Labeled Terminal Phosphate-Linked Nucleotides," Nucleosides, Nucleotides and Nucleic Acids, vol. 27, No. 9, Sep. 2008, 12 pages.

Margulies et al., "Genome sequencing in microfabricated high-density picolitre reactors," Nature, vol. 437, Sep. 15, 2005, 6 pages.

Yang et al., "Nucleoside alpha-thiotriphosphates, polymerases and the exonuclease III analysis of oligonucleotides containing phosphorothioate linkages," Nucleic Acids Research, vol. 35, No. 9, Apr. 22, 2007, pp. 3118-3127.

NIH, "Advanced Sequencing Technology Awards 2012," https://www.genome.gov/27550070, Sep. 14, 2012.

Kumar et al., "PEG-Labeled Nucleotides and Nanopore Detection for Single Molecule DNA Sequencing by Synthesis," Scientific Reports, vol. 2, No. 684, Sep. 21, 2012, pp. 1-8.

Anderson Andrea, "Intel, PacBio Researchers Among Team Taking on Exploratory Project Pairing SMRT Sequencing with Electronic Tags," https://www.genomeweb.com/sequencing/intel-pacbio-researchers-among-team-taking-exploratory-projectpairing-smrt-sequ, Oct. 29, 2012.

Rahman et al., "Chemiluminiscence sensor for high-throughput DNA sequencing," Proceedings of the Eurosensors XXIII conference, 2009, 4 pages.

Nakato et al., "Photoinduced Electron Transfer between Ruthenium-bipyridyl Complex and Methylviologen in Suspensions of Smectite Clays," J. Phys. Chem. C, vol. 116, No. 15, Mar. 30, 2012, pp. 8562-8570.

Torimura et al., "Fluorescence-Quenching Phenomenon by Photoinduced Electron Transfer between a Fluorescent Dye and a Nucleotide Base," Analytical Sciences, vol. 17, Jan. 2001, pp. 155-160.

Vrabel et al., "Base-Modified DNA Labeled by [Ru(bpy)3]2+ and [Os(bpy)3]2+ Complexes: Construction by Polymerase Incorporation of Modified Nucleoside Triphosphates, Electrochemical and Luminescent Properties, and Applications," Chem. Eur. J., 2009, 15, Published online Dec. 15, 2008, pp. 1144-1154.

Merriman et al., "Progress in Ion Torrent semiconductor chip based sequencing," Electrophoresis, 2012, pp. 3397-3417.

International Searching Authority, "Notification of Transmittal of the International Search Report and the Written Opinion of the International Searching Authority," in International Application No. PCT/US2014/066827, dated Feb. 9, 2015,11 pages.

Escalante et al., "Directed assembly of functional light harvesting antenna complexes onto chemically patterned surfaces," Nanotechnology, vol. 19, No. 2, Article No. 025101, 2008, pp. 1-6.

Archon Genomics, "$10 Million Archon Genomics XPrize to Sequence 100 Centenarians' DNA and Announces Medco as Presenting Sponsor," X-prize, New York, Oct. 26, 2011, 5 pages.

Novotny et al., "Antennas for Light," Nature Photonics, vol. 5, 2011, pp. 83-90.

U.S. Department of Energy, "PacBio Sequencing Technology," DOE Joint Genome Institute, 1 page.

Dang, Xiangnan et al., "Tunable Localized Surface Plasmon-Enabled Broadband Light-Harvesting Enhancements for High-Efficiency Panchromatic Dye-Sensitized Solar Cells," Nano Letters, vol. 13, 2013, pp. 637-642.

Kennelly, Theresa, "Evidence for the Formation of a Photoactive Ru(bpy)/3∴2+− EDTA Ion Pair," J. Phys. Chem., vol. 90, 1986, pp. 5338-5339.

Dragnea, Bogdan, "Bio-inspired Materials: Unnatural Life," Nature Materials, vol. 7, 2008, pp. 102-104.

Ohtani, Hiroyuki et al., "Nanosecond Spectroscopy on the Mechanism of the Reduction of Methylviologen Sensitized by Metallophthalocyanine," J. Phys. Chem., vol. 88, 1984, pp. 4431-4435.

Chung et al., "Plasmonic Nanostructures for Nano-Scale Bio-Sensing," Sensors 2011, 11, www.mdpi.com/1424-8220/11/11/10907/pdf, Basel, 2011, pp. 10907-10929.

Ozbay, Ekmel "Plasmonics: Merging Photonics and Electronics at Nanoscale Dimensions," Science, vol. 311 No. 5758 Jan. 13, 2006, pp. 189-193.

University of Illinois, NIH award combines plasmonic light focusing with nanopore technology for DNA sequencing, http://engineering.

(56) References Cited

OTHER PUBLICATIONS illinois.edu/news/article/2013-09-09-nih-award-focuses-nanopore-technology-dna-sequencing, Published online Sep. 9, 2013.
Namasivayam et al., "Advances in on-chip photodetection for applications in miniaturized genetic analysis systems," Journal of Micromechanics and Microengineering, vol. 14, No. 1, Aug. 18, 2003.
Hassibi, Arjang "Biosensor Systems in Standard CMOS: Fact or Function?" https://www.src.org/calendar/e004576/hassibi.pdf, Published online Mar. 22, 2012.
Kinkhabwala et al., "Large single-molecule fluorescence enhancements produced by a bowtie nanoantenna," Nature Photonics 3, Published online Oct. 18, 2009, pp. 654-657.
Punj et al., "A plasmonic 'antenna-in-box' platform for enhanced single-molecule analysis at micromolar concentrations," Nature Nanotechnology 8, Published online Jun. 9, 2013, pp. 512-516.
Taiwan Intellectual Property Office, "Office Action," Taiwan Patent Application No. 103141014 dated May 24, 2016, 13 pages.
International Searching Authority, "International Preliminary Report on Patentability," International Application No. PCT/US2014/066827 dated Jul. 7, 2016.
Taiwan Intellectual Property Office, "Decision of Rejection," Taiwan Patent Application No. 103141014 dated Oct. 14, 2016, 9 pages.
European Patent Office, Extended European Search Report dated May 26, 2017 in European Patent Application No. 14873567.3.
European Patent Office, Communication pursuant to Article 94(3) EPC dated Feb. 2, 2018 in European Patent Application No. 14873567.3.
Korean Intellectual Property Office, Notice of Allowance dated Feb. 2, 2018 in Korean Patent Application No. 2016-7014016.
European Patent Office, Communication pursuant to Article 94(3) EPC dated Jul. 27, 2018 in European Patent Application No. 14 873 567.3, five pages.
Korea Intellectual Property Office, Notice of Preliminary Rejection dated Sep. 14, 2017, in Korean Patent Application No. 2016-7014016.

* cited by examiner

INTEGRATED PHOTONIC ELECTRONIC SENSOR ARRAYS FOR NUCLEIC ACID SEQUENCING

CROSS REFERENCE TO RELATED APPLICATIONS

This application is a continuation of U.S. patent application Ser. No. 14/142,603, filed Dec. 27, 2013. This application also relates to U.S. patent application Ser. No. 13/721,488, filed Dec. 20, 2012. The content of each of the above applications is hereby incorporated by reference.

FIELD OF THE INVENTION

The embodiments of the invention relate generally to electronic sensors and integrated circuit devices, and more specifically to electronic sensor arrays, photonics, light antennas, nucleic acid sequencing, and single molecule nucleic acid sequencing.

BACKGROUND INFORMATION

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The first sequences of DNA (deoxyribonucleic acid) molecules were reported in the early 1970's. The human genome contains more than 3 billion base pairs of DNA. The first whole human genome sequence for an individual was not obtained until 2003, thirty years after the first sequences of DNA were obtained. This first sequence of an entire genome of a human cost about $2.7 billion dollars and took more than ten years to accomplish (according to the National Human Genome Research Institute). Knowledge of an individual's entire genome provides tremendous opportunities to target therapies and medical treatments to individuals most likely to benefit and to understand the molecular basis of many diseases. Forty years after the first DNA molecule was sequenced, the search for a technique that would allow an entire human genome to be rapidly and accurately sequenced cost effectively remains an elusive target.

BRIEF DESCRIPTION OF THE FIGURES

The material described and illustrated herein is provided for purposes of exemplifying aspects of the invention and is not meant to be limiting of the scope of the invention. For simplicity and clarity of illustration, elements illustrated in the figures are not necessarily drawn to scale. Further, where appropriate, reference labels have been repeated among figures to indicate corresponding or analogous elements. In the figures.

DETAILED DESCRIPTION OF THE INVENTION

In the following description, specific details are presented to provide an understanding of embodiments of the invention. Embodiments can be practiced without one or more of these specific details and specific details of one embodiment can in many instances be practiced with other disclosed embodiments, as will be apparent to one of skill in the art. In other instances well-known features are not described in detail in order to not obscure the description.

Devices and methods for molecular detection using electronic sensor arrays that have optional associated optical antennas are described. Electronic detection is combined with optical excitation to determine the presence or identity of an analyte of interest. Embodiments of the invention provide devices and methods that allow highly parallel nucleic acid sequence determination and that offer advantages of accuracy, high throughput, and reasonable costs. However, it should be noted that electronic sensor arrays combined with optical antennas described herein are also useful for other types of analyte detections.

A light harvesting antenna can be a structure that converts photons into plasmons, and which can support plasmonic resonance, focusing of plasmons, or both. Non-limiting examples of structures that can support plasmonic resonance include bow tie structures, spike antennas, and bowtie cross structures; non-limiting examples of structures which can focus plasmons include zero mode waveguides, plasmonic waveguides and bullseye antennas; non-limiting examples of structures which provide both plasmon focusing and plasmonic resonance include bullseye antennas with central apertures. Structures can be optimized for a single wavelength, or can be optimized for two or more wavelengths, for example by optimizing orthogonal bow tie antennas for different wavelengths. Structures can be fabricated by the selective etching or deposition to from either positive structures such as bow tie antennas, or negative structures such as a zero mode waveguides. A light harvesting structure, for example, a bow tie antenna, can be fabricated on a planar surface, or can be a structure which can be a formed as structure separate from a planar surface, in such non-limiting examples such as nano-rice, and nano-crescents.

Figure 1A:
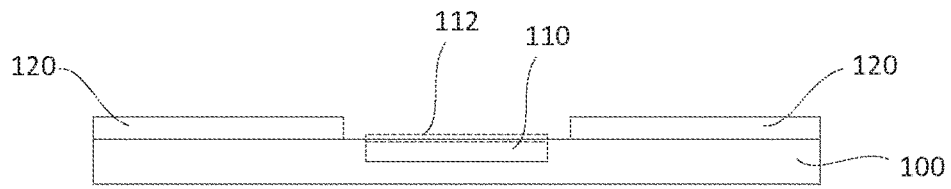
FIGS. 1A-D are schematic diagrams illustrating a view of a sensor region and associated optical antennas and views of an array of sensors that have associated optical antennas.

FIGS. 1A-D provide views of an exemplary device in which a substrate 100 incorporates sensors 110 and light harvesting antennas 120. FIG. 1A is a cutaway view along line 1-1 of FIG. 1B. In embodiments of the invention, the substrate 100 comprises an electronic chip (an integrated circuit or IC chip), such as a CMOS (complementary metal-oxide-semiconductor) chip, and the substrate 100 comprises electronics (not shown) that are operably coupled to the sensors (or transducers) 110 and are capable of performing one or more of the following functions: individually addressing, driving, amplifying a signal from, collecting data from, and analyzing data from the sensors 110. In alternate embodiments, one or more of the following: individually addressing, driving, amplifying a signal from, collecting data from, and analyzing data from the sensors 110 is performed by external electronics, one or more computers, or a combination thereof. Although the sensors 110 are shown as having a square surface, other shapes and relative sizes are also possible. For example, the sensor 110 surface could be circular, oval, rectangular, or another type of multisided figure, such as a hexagon or a pentagon. Sensors 110 are electronic sensors or transducers that are capable of converting a physical event into an electronic signal. In embodiments of the invention, the physical event is an electron transfer event. In FIG. 1A, the sensor surface comprises optional sensor coating layer or layers 112. The optional layer or layers 112 is/are described more fully herein. The optional sensor coating layer or layers 112 can also be a layer that only partially covers the sensor 110 surface. In some embodiments a protective layer (not shown) can be used to prevent attachment of immobilized enzymes in positions in which the excited states of bound photosensitizer-labeled nucleotides can be quenched in an unwanted manner by a metal structure, resulting in a transfer of the electron to a metal structure, or transfer of the excited state energy to the metal structure. An optional layer can be of a dielectric material, which can be from 5 to 20 nm thick so as to space the photosensitizer labeled molecules away from the metal structure.

Figure 1B:
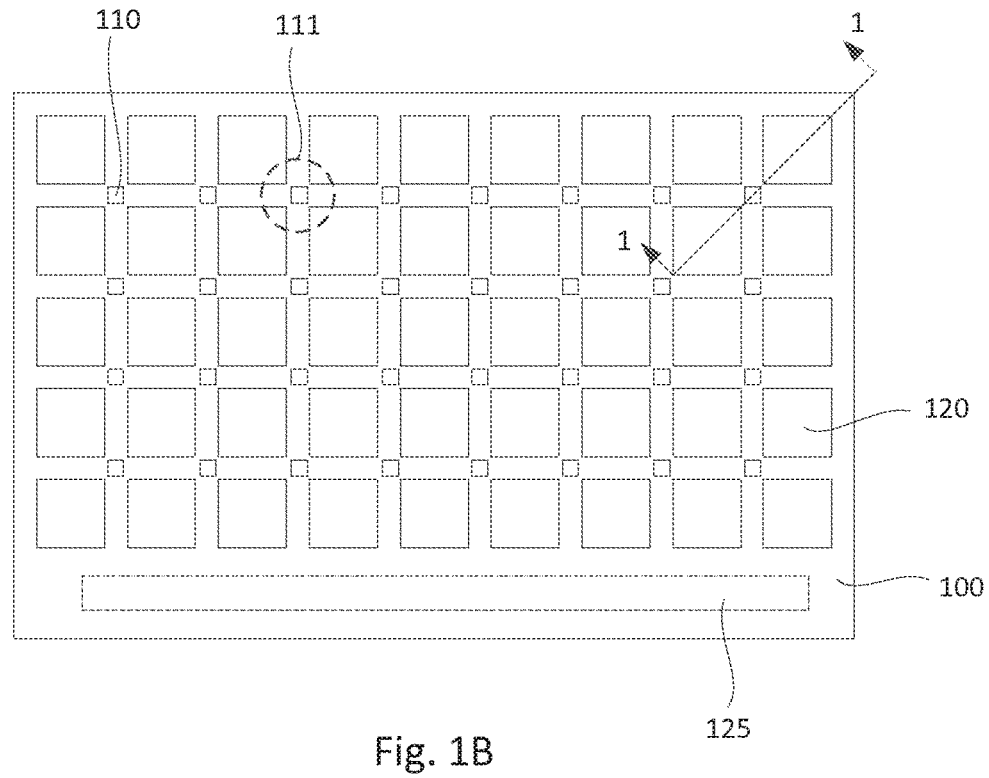
Figure 1C:
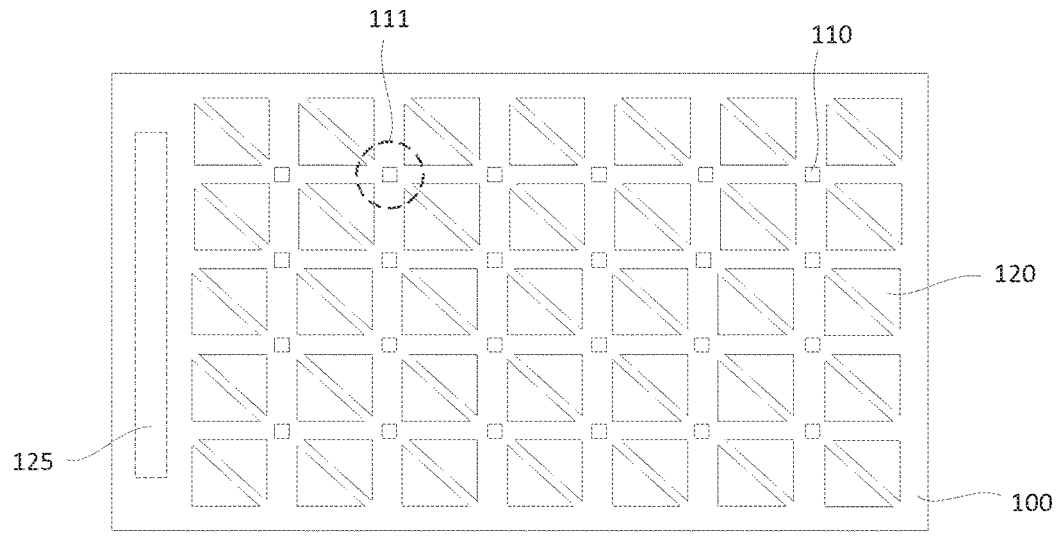
Figure 1D:
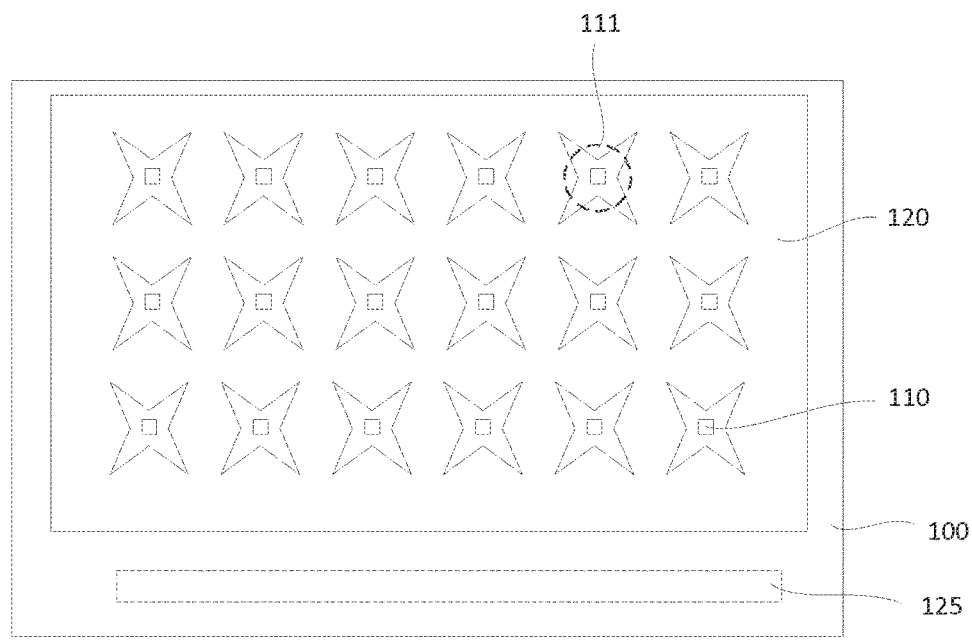

In embodiments of the invention, light harvesting antennas 120 are capable of concentrating light and converting photons into plasmons. Surface plasmons form especially at the corners of the antennas 120 and the intensity of the electric field associated with the plasmons is increased in the junction of two or more light antennas or between portions of a single antenna which interact, as can occur with an antenna structure formed as an aperture in a planar metal layer. FIGS. 1B-D illustrate some exemplary shapes that light harvesting antennas 120 can be configured in. Other shapes and relative numbers (relative to numbers of sensors 110) of antennas 120 are also possible. As can be seen in FIG. 1C relative to FIGS. 1B and 1D, for example, different numbers of antennas 120 per sensor are possible. Antennas 120 are configured to provide surface plasmons to molecules to be analyzed located in the sensor region and at least one antenna 120 is associated with a sensor 110. A reaction (or sensor) region 111 has one or more associated light harvesting antennas 120. Light harvesting antennas 120 are comprised, for example of a thin layer of metal, such as, gold, silver, aluminum, platinum, zinc, copper other coinage metals or alloys thereof. In embodiments of the invention, the light harvesting antennas 120 comprise a nanoscale layer of material, for example, the thickness of the light harvesting antennas 120 can be 20 to 100 nm or a number greater than 100 nm. In FIG. 1D the array of light harvesting antennas 120 can be formed such that the antennas have one or more boundaries in common and the sensors 110 are located in cut-out regions of the antenna material.

Optionally, one or more counter and/or reference electrodes 125 are located, in or on the substrate 100 surface. Although one counter or reference electrode 125 is shown in FIGS. 1B-D, other shapes, sizes, locations, and numbers of the counter and/or reference electrodes 125 are possible. In alternate optional embodiments, one or more counter electrodes are located in the solution that is employed to provide reactants to the sensor region. One or more reference electrodes can also be provided in the solution that is employed to provide reactants to the sensor regions. Counter and reference electrodes are useful in embodiments where current, voltage, capacitance, and/or resistance are measured by an electrode sensor.

Other light harvesting structures, such as for example, as a zero mode waveguides, can also be used with the sensors and methods described herein.

Figure 2A:
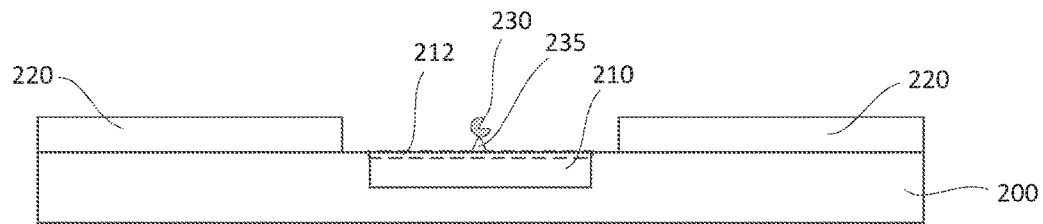
FIGS. 2A-E illustrate additional sensor regions that have associated optical antennas and immobilized molecules.
Figure 2B:
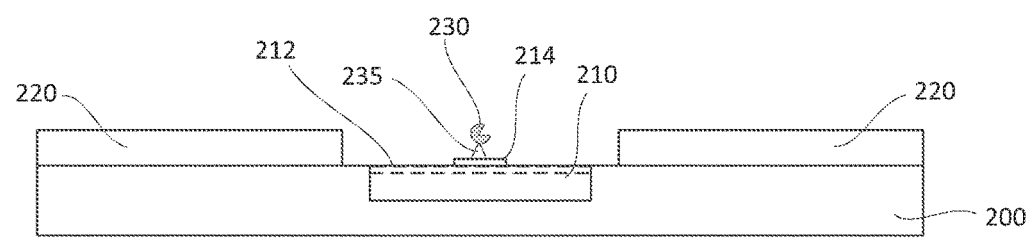
Figure 2C:
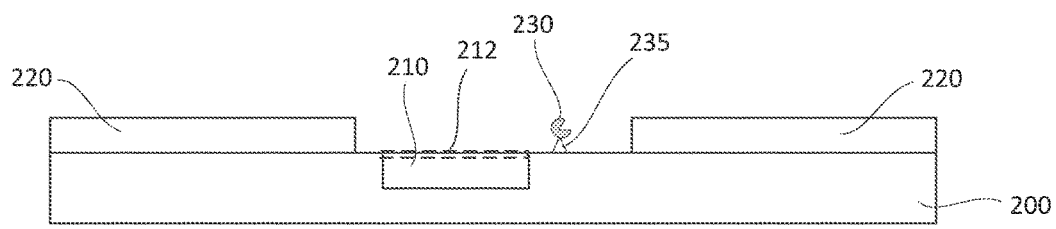
Figure 2D:
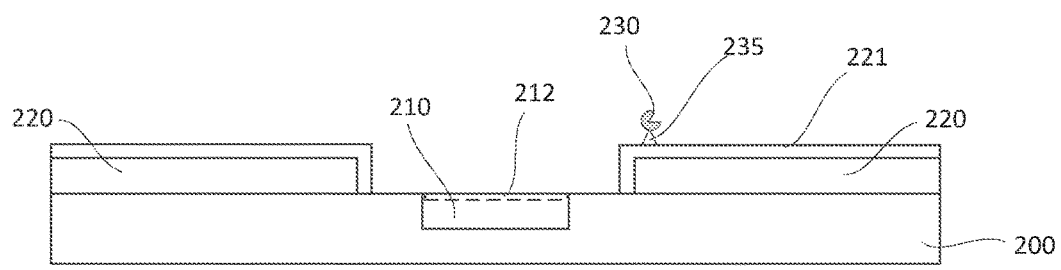
Figure 2E:
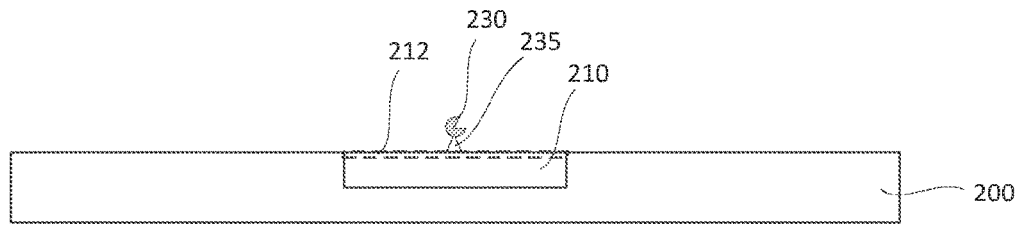

FIGS. 2A-E show light harvesting antennas and sensor regions that have immobilized enzymes according to embodiments of the invention. In FIGS. 2A-D, substrate 200 comprises a sensor 210 and light harvesting antennas 220. In FIGS. 2A-E, one sensor 210 and two light harvesting antennas 220 of an array of sensors and antennas are shown. In FIGS. 2A, 2C, 2D, and 2E the sensor surface comprises optional sensor coating layer or layers 212 to facilitate molecular attachment and/or protect sensor surfaces. In some embodiments, an optional protection layer (not shown) can be used to prevent attachment of immobilized enzymes in positions where undesired quenching of bound photosensitizer-labeled nucleotide can occur through proximity to a metal. An optional protection layer can be of a dielectric material. In alternate embodiments, one or more sensor coating layers 212 can extend beyond the surface of the sensor 210 and also cover the antennas 220. In FIG. 2B the sensor surface comprises a partial layer or molecular attachment pad 214 of a material to facilitate molecular attachment. The molecular attachment pad 214 of FIG. 2B is also usable in the device of FIGS. 2C-E and can be larger or smaller than the pad or partial layer shown. In FIG. 2D, an optional protective layer 221 coats antennas 220 and can be, for example, a dielectric material. In FIG. 2E, a sensor 210 does not have associated light harvesting antennas. In embodiments with or without light harvesting antennas, light can be directed to sensor regions using lenslet arrays, Fresnel lenses, or lenses, for example. The sensor region of FIG. 2E can have a partial layer or molecular attachment pad of FIG. 2B and/or the enzyme attachment of FIG. 2C. In other embodiments, lenslet arrays, Fresnel lenses, or lenses are used localize light in combination with light gathering antennas.

In FIGS. 2A-E a substrate 200 comprises an electronic chip (an IC chip), such as a CMOS (complementary metal-oxide-semiconductor) chip, and the substrate 200 incorporates electronics (not shown) that are operably coupled to the sensors 210 and are for one or more of the following functions: individually addressing, driving, amplifying data from, collecting data from, and analyzing data from the sensors 210. In alternate embodiments, one or more of the following: individually addressing, driving, amplifying a signal from, collecting data from, and analyzing data from the sensors 210 is performed by external electronics, one or more computers, or a combination thereof.

One or more enzymes 230 are located in the sensor region and are attached to a surface of the sensor region through optional linker 235. In embodiments of the invention, the enzyme 230 is, for example, a DNA polymerase, a RNA polymerase, a terminal transferase, a reverse transcriptase, or a telomerase. Linkers 235 for anchoring the enzyme 230 to the sensor region include, for example, PEG (poly ethylene glycol), a carbonyl linker, a straight chain carbon linker, a photoactivatable linker, or a chemically cleavable linker, or another appropriate linker. Linkers 235 can be attached to a surface or a modified surface, such as a surface having a layer, a coating, a chemical modification, or a combination thereof, inside the reaction region. In alternate embodiments, linkers 235 are not present and the enzyme 230 is attached directly to a surface inside the sensor region. In FIG. 2D, the enzyme 230 and/or optional linker 235 can be attached to the antenna through photo-attachment, where light activation of the antenna facilitates the attachment. In embodiments of the invention, one enzyme 230 is present in one sensor region for each of the sensors of an array for at least part of the array. In embodiments of the invention, the number of sensor regions with a single enzyme present is greater than achievable with a Poisson distribution. One enzyme per sensor region of an array can be achieved, for example, in a statistical manner, using a Poisson distribution. Statistically a maximal number of sensors with one enzyme per sensor region is obtained, for example, by controlling the concentration of linker or controlling the concentration of enzyme during surface attachment so that statistically one enzyme is attached per sensor region. Embodiments where statistically a maximal number of sensors with one enzyme present on one sensor in an array, are said to have one enzyme per sensor herein, however, it will be understood by one of skill in the art that there are be a percentage of sensors in the array where this is not true. Data from sensor regions that do not contain an enzyme or contain more than one enzyme are detected (regions containing no enzyme or more than one enzyme return no signal or have an increased signal relative to one enzyme sensor regions, respectively) and can be discarded or can be used as controls for nucleic acid sequencing purposes.

In alternate embodiments, more than one enzyme can be present per sensor region. In embodiments of the invention, uniquely identifiable photosensitizer labels are resolved by the different responses of the sensing region of the same sensor (transducer).

Optionally, one or more counter and/or reference electrodes (not shown) are provided in or on the substrate 200 surface as in FIGS. 1A-D. In alternate optional embodiments, counter and/or reference electrodes are provided in the solution that is employed to provide reactants to the sensor regions. Counter and reference electrodes are useful in embodiments where current, voltage, or resistance is measured by an electrode sensor.

In embodiments of the invention, the sensor region (or reaction region) comprises an electronic sensor and the area of the sensor surface proximate to and surrounding the sensor. In embodiments of the invention, a reaction region (or sensor region) is a region within the plasmonic enhancement region of one or more light harvesting antennas. In the sensor region, an immobilized polymerase can be complexed with a partially double stranded nucleic acid and a reaction in which nucleotides are polymerized to a nucleic acid strand can occur. In other embodiments, a reaction region is a region in which an immobilized polymerase complexed with a partially double stranded nucleic acid can be bound or affixed and it comprises a flood illumination field, or the field of a light beam formed by a lens or lenslet, which can be a part of a lenslet array. In embodiments of the invention, the sensor region fits within the area on the surface wherein light energy is focused by lenslets, and or focusing light-harvesting antennas, and or energy is caused to resonate by plasmonic resonance by light harvesting antennas. In embodiments of the invention, the sensor region is 12 to 15 nm, 15 to 20 nm, 12 to 50 nm, 12 to 100 nm, or 100 nm to 500 nm wide in its widest dimension. In embodiments of the invention, the sensor surface is 10 to 50 nm, 10 to 100 nm, or 10 nm to 1 µm wide in its widest dimension. The sensor region can include the sensor surface and an area of the substrate surface surrounding the sensor that extends 10 to 30% beyond the sensor surface area.

In some embodiments the sensor region can have a dielectric or semiconductor layer over the metal of the light harvesting antennas so as to prevent metal quenching of the energy absorbed by the photosensitizer label. The sensor region has one or more light harvesting antennas positioned so that localized energy (originating from radiant light) is directed into the sensor region. Other numbers of light harvesting antennas associated with a sensor region are possible, for example, FIG. 1B illustrates four light harvesting antennas associated with a sensor region and FIG. 1C illustrates eight light harvesting antennas associated with a sensor region. Light interaction with light-harvesting antennas is typically a function of the polarization of the light; two or more different light wavelengths can interact with the same set of antennas in an effectively orthogonal manner, wherein a first illumination light of one wavelength can have one polarization, and can interact with one set of antennas to focus plasmons and or to generate plasmonic resonances, while a second illumination light of another wavelength with a polarization orthogonal to the first illumination light can interact with a second set of antennas configured for focusing plasmons and or plasmonic resonance orthogonal to the first set of antennas. A light harvesting antenna is a structure that converts optical radiation into localized energy (surface plasmons). One light harvesting antenna can be associated with more than one sensor region. Light harvesting antennas can be sized differently so as to allow light of different wavelengths to absorb photons of different energies and permit input light sources of the same or similar polarizations to interact with different light harvesting antennas.

Types of electronic sensors useful in embodiments of the invention include, for example, field effect transistors (FETs), ion selective transducers, ion sensitive field effect transistors, chemical field effect transistors, extended gate FETs, high band gap semiconductor coated electrochemical transducers, electrochemical transducers, potentiometric sensors, and electrode transducers. In embodiments of the invention, sensors have a sampling rate of greater than 1 KHz and, for sensors measuring current, a detection sensitivity of less than 1 pA. Floating gate field effect transistors, which can be extended gate floating gate field effect transistors, respond to changes in the electric charge on or proximate to the sensor surface, which change the charge distribution in the channel of the FET, and thus the characteristics of current passing through the channel of the FET. Electrodes are capable of measuring current, voltage, capacitance, and resistance changes at the sensor surface. The sensor can be conductive or semiconductive and can be comprised of materials, such as, for example, Au, Ag, Pt, or alloys of Au, Ag, and/or Pt, conductive carbon materials, such as doped diamond materials, semiconducting materials such as $TiO_2$, ITO (indium tin oxide), $Ta_2O_5$, and ZnO, organic semiconductor materials, and high band gap semiconductor materials such as boron doped diamond, aluminum, gallium and boron nitrides, and silicon carbide.

Figure 3A:
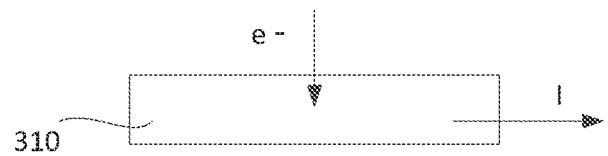
FIGS. 3A-D show modes for electrical signal detection at a sensor surface.
Figure 3B:
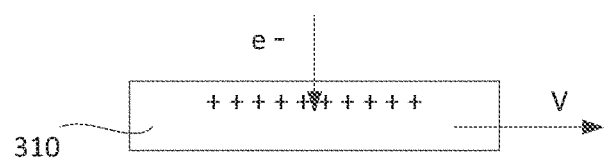
Figure 3C:
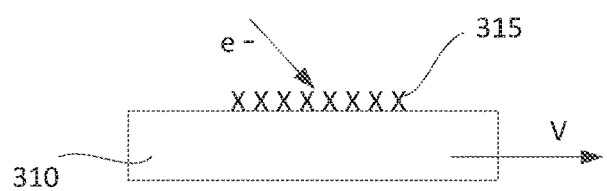
Figure 3D:
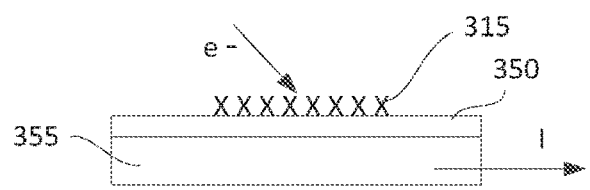

FIGS. 3A-D diagram electronic signal detection schemes useful for detecting molecular sequencing reactions according to embodiments of the invention. In FIG. 3A a sensor 310 is a high band gap semiconductor coated electrode, a dielectric coated electrode, or an electrode comprised of a conducting material. In operation, an electron (e) is transferred from the reaction region, either directly from a photosensitizer moiety or as a part of an electron transfer chain, and output from the sensor 310 as current. A change in current at the sensor can indicate the presence of the photosensitizer moiety bound to the immobilized enzyme. In this mode, electrons travel through the sensor 310. Although current is shown flowing out of the sensor region in a particular direction in FIG. 3A, other directions for current flow are also possible, and depend on how the sensor is electrically configured within the substrate (not shown). FIG. 3B illustrates an electron-hole recombination detection scheme at sensor 310. In FIG. 3B, electrons are injected into a semiconductor portion of a sensor, recombine with holes, and are detected through capacitive, voltage, or current changes at the sensor. Electrons can be injected into a semiconductor. FIG. 3C illustrates a sensor 310 that has one or more surface-attached electron acceptors 315. In the detection scheme shown in FIG. 3C, electrons from the reaction region reduce the surface-attached electron acceptors 315 and the reduced electron acceptors 315 are detected as a potential difference at the surface of the sensor. In alternate embodiments, surface-attached molecules 315 are electron donors. A potential difference at the surface of the sensor, which can result from a current change in an ISFET or CHEMFET sensor, or can be detected as a potential change or current change in an electrochemical sensor, or can be detected as a change in capacitance using a potentiometric sensor. In alternative embodiments, electrons can be supplied to the reaction region from oxidation of the surface-attached electron donors 315 and the oxidized electron donors 315 are detected as a potential difference at the surface of the sensor. In embodiments of the invention, electron acceptors are molecules that are capable of being reversibly reduced. In alternate embodiments, electron acceptors are capable of being reduced, but the electron transfer is not reversible. FIG. 3D illustrates parts of a field effect transistor having surface-attached electron acceptors/donors 315 on the gate region layer 350 of the FET. The gate region layer 350 is at least in part above the channel region 355 of the FET, although the gate can be larger than the channel, and the gate region of FET includes the attached electron acceptors/donors 315. Electrons generated in the reaction region reduce surface-attached electron acceptors 315 and the increased negative potential of the surface of the FET 315 is detected as a change in current flow through the channel region 355. Alternately, electrons are supplied in the reaction region by surface-attached electron donors 315 and the increased positive potential of the surface of the FET can be detected as a change in current flow through the channel region 355. Compounds and molecules useful as surface-attached electron acceptors 315, include, for example, $Ru(bpy)_3^{2+}$, other metal containing complexes such as $Rh(bpy)_3^{2+}$, $Fe(bpy)_3^{2+}$, or $Co(bpy)_3^{2+}$, or other photosensitizers which can be bound by a polymerase which is attached to a surface of the sensor, or a mediator in an electron transfer chain such as methyl viologen, other viologens, or other mediators. Exemplary electron donors include, hydroxyl-containing amines, carboxyl-containing amines, such as glycine, and triethanolamine.

In embodiments in which the sensor is an extended gate FET, a metal electrode (not shown) becomes the extended gate of the FET device. A FET-based device comprises a channel that is typically comprised of a doped semiconductor material coated with a thin layer of insulating material (such as, for example, silicon dioxide, silicon nitride, aluminum nitride, and or silicon oxynitride). The channel of the FET, can be comprised of a P- or N-type semiconductor, as is well known in the art, such as for example, silicon or germanium doped with boron, arsenic, phosphorous, or antimony.

Electrode sensors can include one or more sensor coating layer or layers. Sensor coating layers include a coating of a metal oxide, a semiconductor or semiconductor oxide, or a dielectric. Electrode sensors comprised of platinum or any other electrochemically active material such as, for example, diamond, gold, ITO, iridium oxide, or an alloy thereof, can be coated with a thin dielectric (or semiconducting) film comprised of a material such as, for example, $Ta_2O_5$, $TiO_2$, $SiO_2$, $Y_2O_3$, $Al_2O_3$, $HfO_2$, $ZrO_2$, $ZrSiO_4$, $BaTiO_3$, $BaZrO_3$, or $Si_3N_4$. In embodiments of the invention, the film is between 0 to 7 nm thick. Electrode sensors can also be coated with a well-defined or self-assembled monolayer or with very thin multiple layers of hydrophilic and biocompatible organic compounds, polymers, or biopolymers, for example, with polyethylene glycols, anilines, phosphonates, thiols, aza-adenine, poly-adenosine(polyA), mercaptoundecanol (Thiol-C11OH), or peptides, to reduce or prevent entirely catalytic reaction of the transducer material with the solution and or solution additives and reduce adsorption of the redox tags, without significantly reducing the electron transfer at the reducing and oxidizing electrodes. In one such embodiment, the organic or biomolecular coating possesses a low energy barrier to enable electron tunneling or hopping through or over the energy barrier to maintain a similar (e.g., 90 to 100%) electron transfer rate as with bare electrodes. In embodiments, the coating is non-catalytic and non-electrochemically active (or with reduced catalytic and electrochemical activity) and can also be used as a protective film to reduce fouling or denaturing of the electrode during operation. Additional molecules and compounds such as, tetra-DTT phosphates and tetra-DTT-ferrocene phosphates, alendronate derivatives, thiol compounds and thiol-containing polymers can be used as a surface coating molecules. Further, electrode materials and coating layers are described in U.S. patent application Ser. No. 14/104,546 filed Dec. 12, 2013 and entitled, "Highly Selective Coated Electrode Nanogap Transducers for the Detection of Redox Molecules," which is incorporated by reference herein.

Substrate, sensor, sensor coating, and electrode materials, such as metals, metal oxides, and $SiO_2$, have, in many instances, surface-attached —OH groups that are available for further reaction and molecular coupling. Additionally, optional layers can be used to facilitate attachment, for example, polymers such as polystyrene, poly vinyl alcohol, polyacrylamide, or another appropriate polymer can be used. An attachment facilitation layer can be further functionalized to permit binding to the layer, with binding agents such as biotin, avidin, streptavidin, modified PEG, or other appropriate agents or modifications to the attachment facilitation surface. Further, surfaces that present —OH groups for molecular coupling are optionally created on substrate surfaces through, for example, creating a thin oxide layer on a metal or semiconductor (such as through chemical or plasma etching processes or by exposure to atmospheric oxygen) or through depositing a thin layer or region of $SiO_2$ onto the surface. Areas of the reaction region that can present —OH containing or $SiO_2$ surfaces for molecular attachment include, the surfaces of sensors, the surface of the substrate surrounding the sensor, or full or partial layers, pads, or coatings on sensor surfaces or on the areas of the substrate that surround the sensor (the sensor region). For surfaces of $SiO_2$ or surfaces of metals having available —OH groups, molecules are optionally attached to the surface through the use of silane linkers (organo silane compounds). In general, silane linkers are molecules that contain silicon. Useful silane molecules include ones that have at least two different reactive groups bonded to the silane atom of the molecule: Y—R—Si—(X)$_2$. One of the reactive groups, the group represented as X, is capable of bonding to inorganic materials such as $SiO_2$ and metals. These functional groups that are capable of bonding to inorganic materials are groups such as methoxy, ethoxy, chlorine, and silanolic hydroxyl groups. The second functional group, the group represented as Y, is a group such as a vinyl, an epoxy, a methacryl, an amino, a mercapto, or a carboxylic acid group that is capable of forming a chemical bond to an organic material (such as a monomer used to form a polymer). The R group is typically an organic group comprised of from 1 to 10 carbon atoms, such as a straight chain or branched alkane but can also include alkene or alkyne groups, and can include alcohols or other functional groups. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules.

Areas functionalized with, for example, one of or a combination of molecules containing amine, aldehyde, epxoy, or thiol groups are capable of attaching molecules having amine functional groups (for surfaces bearing carboxy, epoxy, and/or aldehyde functional groups) or carboxyl functional groups (for surfaces bearing amine groups). Additionally, molecules having thiol groups can be used to facilitate molecular attachment to gold or other noble metal surfaces. Various conjugation chemistries are available to join the functional groups (for example, EDC for amine-carboxyl). The concentration of molecules on the substrate surface can be controlled, for example, in several ways: by limiting the density of surface functional groups or by limiting the quantity of molecules to be attached.

A system for molecular sequencing, including one or more arrays of sensors and one or more arrays of light harvesting antennas, one or more light sources, optics (such as lenslet arrays, Fresnel lenses, or other lenses), electronics for driving the sensors and recording measurements, and a computer for recording and analyzing data, also optionally includes fluidic systems that are capable of delivering fluids to the reaction regions. A fluidic system can comprise reservoirs for reagents and washing solutions, pumps and mixing chambers, waste chambers, and fluid delivery systems that deliver fluids to the reaction regions of an array of sensors. In embodiments of the invention, some or all of the electronics for driving the sensors and recording measurements are housed in the substrate with the array of sensors and are operably coupled to the sensors in a manner that allows the sensors to be addressed individually. Light sources useful in embodiments of the present invention include, for example, LEDs, which can be nominally single color LEDs, white light LEDs, multicolor LEDs, single or multi line lasers, arc lamps, which can be wide spectrum sources or can have line spectra. Sources which are wide spectrum sources can be filtered so as to provide appropriate ranges of light wavelengths. Such filtration can be effectuated by the use of gratings, interference filters, or absorption filters or a combination thereof.

In embodiments of the invention, sensors are arrays of individually-addressable transducers. Sensor arrays can be built having a variety of dimensions and numbers of sensors. The selection of numbers and layout of sensors is informed by factors such as, for example, the types and numbers of analytes to be detected, the size of the sensor regions, and costs involved in manufacturing the arrays. For example, arrays of sensors are 10×10, 100×200, 1,000×5,000, $10^4 \times 10^4$, $10^5 \times 10^5$, and $10^6 \times 10^6$. Other array dimensions are also possible. Very high density, high density, moderate density, low density, or very low density arrays can be made. Some ranges for very high-density arrays are from about 100,000,000 to about 100,000,000,000 sensors per array. High-density arrays range from about 1,000,000 to about 100,000,000 sensors. Moderate density arrays range from about 10,000 to about 100,000 sensors. Low-density arrays are generally less than 10,000 sensors. Very low-density arrays are less than 1,000 sensors.

An array of individually addressable sensors can be housed on and electrically coupled to an IC chip (a CMOS chip). In embodiments of the invention, the surface of the chip also comprises sensor-associated light harvesting antennas. The IC chip is typically built on a semiconductor substrate, such as, a semiconductor wafer that is diced apart to yield individual IC chips. The base substrate on which an IC chip is built is typically a silicon wafer, although embodiments of the invention are not dependent on the type of substrate used. The substrate could also be comprised of germanium, indium antimonide, lead telluride, indium arsenide, indium phosphide, gallium arsenide, gallium antimonide, and/or other group III-V materials either alone or in combination with silicon or silicon dioxide or other insulating materials. Layers and layers comprising devices can also be described as the substrate or part of the substrate on which embodiments of the invention are housed or fabricated.

The sensor arrays allow a large number of nucleic acid molecules to be sequenced simultaneously, although other uses are also possible. Methods are provided for sequencing nucleic acids in which amplification of the nucleic acid sample (i.e., increasing the number of copies of the nucleic acid molecules in the sample) optionally does not have to occur.

Figure 4A:
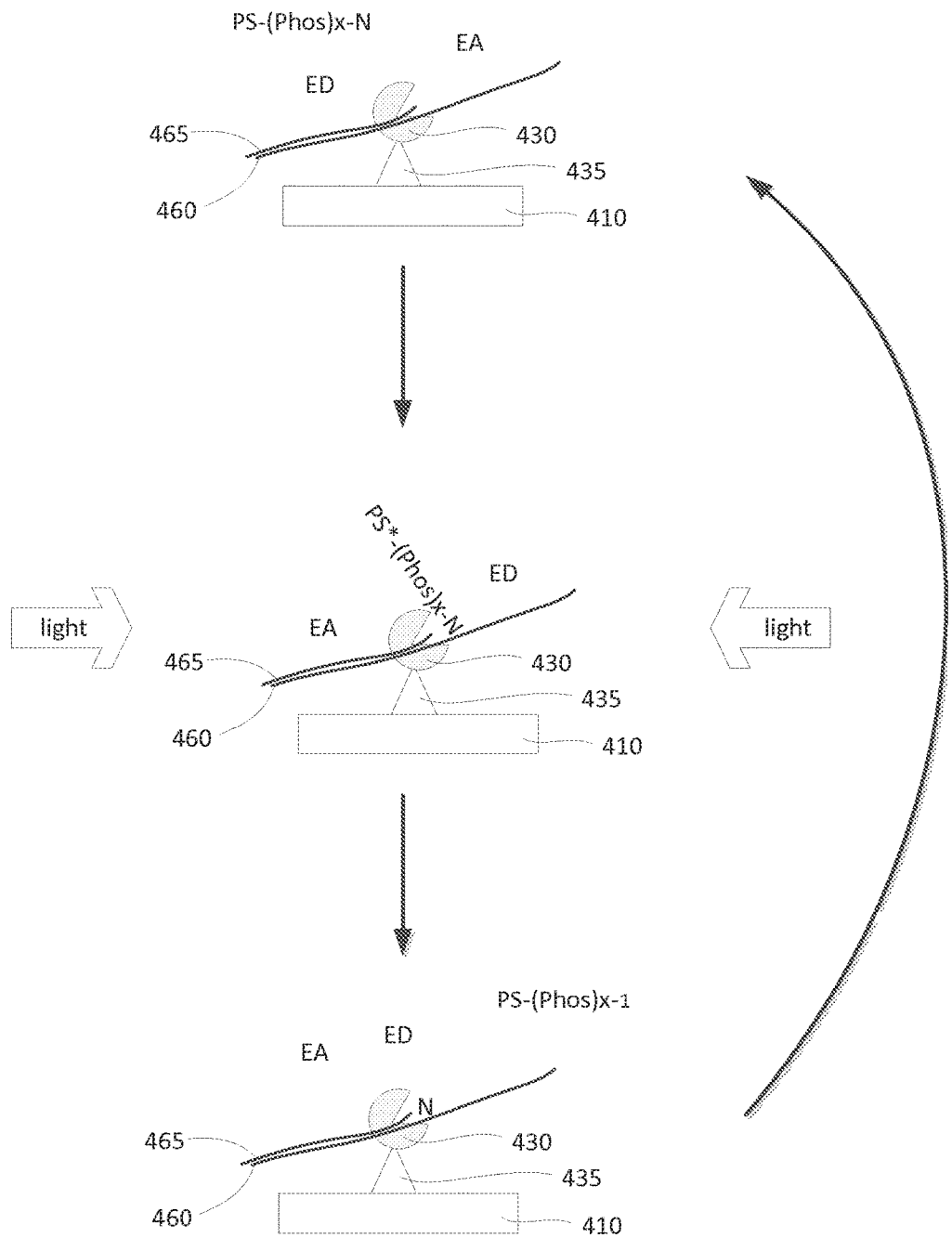
FIGS. 4A-B illustrate schematically a nucleic acid sequencing reaction using an electronic sensor and a photosensitizer-labeled nucleotide.
Figure 4B:
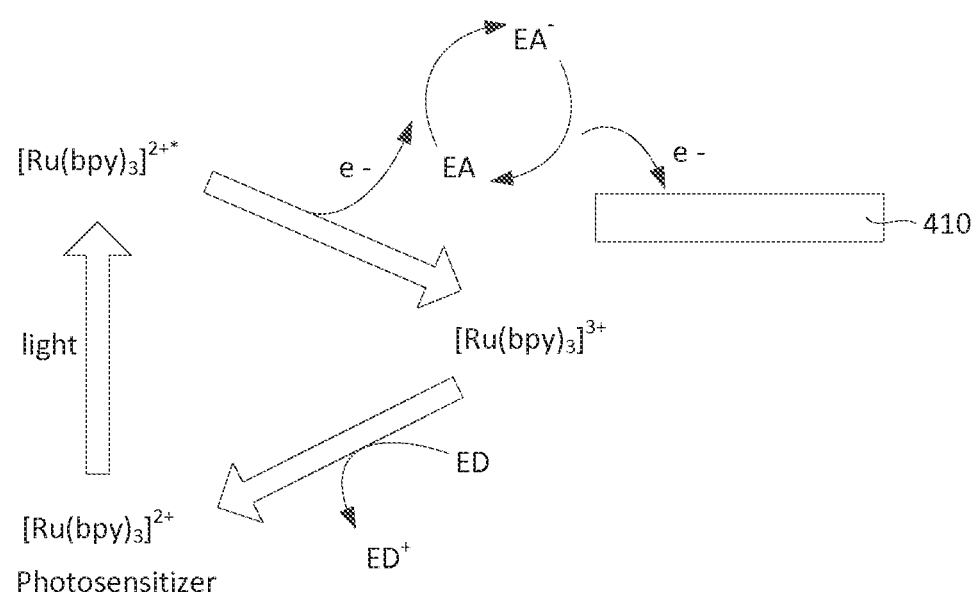

FIGS. 4A-B illustrate a nucleic acid sequencing method in which the presence of a photosensitizer-labeled nucleotide is detected by an electronic sensor. In FIG. 4A, a sensor 410 region has an enzyme 430 immobilized through a linker 435. In embodiments of the invention, the enzyme 430 is a DNA polymerase. The sensor 410 is part of a larger array of sensors (not shown) that also optionally comprises light harvesting antennas (not shown). The sensor 410, the enzyme 430, the linker 435, the array of sensors, and the light harvesting antennas, can be, for example, those described as embodiments of the invention with respect to FIGS. 1A-D, 2A-E, and 3A-D. In FIG. 4A, the immobilized polymerase 430 is complexed with a DNA molecule to be sequenced 460 comprising a hybridized DNA primer 465, which can be a targeted primer, a universal primer, or a hairpin primer. A photosensitizer (PS) labeled nucleotide (PS-(Phos)$_x$N) is added to the solution (not shown) that is in contact with the immobilized polymerase 430. The assay can be a competitive assay (either synchronous or asynchronous) wherein multiple uniquely identifiable photosensitizer-labeled nucleotides are provided at once, or can be a competitive synchronous assay wherein a single uniquely identifiable photosensitizer-labeled nucleotide is provided with the other three nucleotides, which can be incorporatable nucleotides. If the photosensitizer-labeled nucleotide is complementary to the next base of the nucleic acid molecule to be sequenced 460 it binds to the polymerase-nucleic acid molecule complex for a longer period of time than if the photosensitizer-labeled nucleotide is not complementary to the next base of the nucleic acid molecule to be sequenced. The bound photosensitizer label is excited by illuminating light energy, which can be in the form of plasmons concentrated and or recycled by plasmonic resonance by the light harvesting antennas (not shown) from a light source (not shown). The residence time for un-complexed photosensitizer-labeled nucleotides in the detection cavity is significantly less (microseconds) than the residence time for complexed photosensitizer-labeled nucleotides (milliseconds), as diffusion in and out makes binding times by the polymerase of non-complementary nucleotides, extremely short. If photosensitizer-labeled nucleotides are bound by the polymerase, but are not able to be incorporated, either because the nucleotides are unincorporatable nucleotides such as ribonucleotides when using a DNA polymerase, or when the polymerase is provided with insufficient magnesium and or manganese, but is instead provided with an alternative ion, such as calcium, which binds in the metal catalytic region of the polymerase but does not catalyze polymerization, the binding time can be much longer, and can be seconds or many seconds.

In embodiments where the photosensitizer-labeled nucleotide is incorporated by the polymerase, the label can be retained if the label is not bound to the nucleotide through the phosphate chain, and detection can occur at any time prior to cleavage of the photosensitizer label; in embodiments where the photosensitizer label is bound to the nucleotide through the phosphate chain, the label is detectable prior to incorporation of the nucleotide.

In embodiments of the invention, the labeled nucleotide binding event can be detected as illustrated in FIG. 4B. The excited photosensitizer (in this embodiment, $Ru(bpy)_3^{2+*}$) donates an electron to the electron acceptor (EA) which in turn transfers an electron to the sensor 410 or a layer of electron acceptors on the sensor 410 where the electron transfer event is detected by the sensor 410. The oxidized $Ru(bpy)_3^{3+}$ is reduced by the electron donor (ED) back to $Ru(bpy)_3^{2+}$ where it is again excited to $Ru(bpy)_3^{2+*}$ by the concentrated light energy from the light harvesting antennas and is able to transfer an electron to the electron acceptor (EA). In some embodiments, the immobilized polymerase 430 can transiently hold the photosensitizer-labeled nucleotide in place for as long as milliseconds. The binding duration of the photosensitizer-labeled nucleotide with the immobilized polymerase 430 allows a plurality of electrons to be generated during the binding event and a current detectable by the sensor 410 to be produced. In other embodiments, electron donors are associated with the sensor surface, and changes in charge or current are detected as a result of oxidation of the electron donor.

A photosensitizer is capable of absorbing illuminating light energy, which can be in the form of plasmons concentrated and or recycled by plasmonic resonance by the light harvesting antennas from a light source and transitioning into an excited state. The excited photosensitizer is capable of being oxidized reversibly or irreversibly.

An asynchronous sequencing system that employs a sensor 410 that has a detection rate of greater than 1 KHz, for example a detection rate of 10 KHz, can resolve single base incorporation events at a rate of many bases per second. At this rate, a sensor array of 1 million sensors can potentially generate data equivalent to 10× of a human genome sequence ($3 \times 10^9$ bases) in an hour. In other systems, which use a synchronous chemistry and concomitant reagent deliveries with chemistry cycle times of less than a minute, with a sensor array size of 100 million sensors, data equivalent to a 10X human genome can be generated in five hours. An electron donor or an electron acceptor is capable of reversibly donating an electron, or can be provided in an ongoing manner in sufficient numbers so as to replenish the supply of donors.

Referring back to FIG. 4A, in some embodiments, after the complementary photosensitizer-labeled nucleotide binds to the polymerase-nucleic acid molecule complex, the photosensitizer is cleaved from the newly incorporated base with the cleaved phosphates $(Phos)_{x-1}$. The sequencing reaction can then repeat to incorporate a nucleotide complementary to the next base of the nucleic acid molecule to be sequenced 460. The sequencing reactions can repeat until the single-stranded nucleic acid template (molecule to be sequenced) is copied into a double-stranded nucleic acid. In further embodiments, wherein the template comprises circularized nucleic acids, the polymerization can be continued until a desired number of repetitions around the circle are completed.

In embodiments of the invention, the electron acceptor is, for example, bipyridium derivatives of 4,4-bipyridyl such as methyl viologen, ethyl viologen, betaine viologen, benzyl viologen, extended viologens where aryl, ethylene, or thiophene groups can be conjugated between the two pyridine groups. Different electron acceptors and donors can be used with different photosensitizers as appropriate to align with the needed redox potentials of the photosensitizers and working electrodes. Photosensitizer labels can contain one or more photosensitizer moieties. Exemplary photosensitizers include dyes, such as lanthanide dyes as europium cored 4-(4-(4-(2-ethylhexyl-oxy)phenyl) naphthalen1-yl)benzoic acid, or metal-containing complexes, such as $Ru(bpy)_3^{2+}$, derivatives of $Ru(bpy)_3^{2+}$, $Cr(bpy)_3^{2+}$, $Fe(bpy)_3^{2+}$, $Co(bpy)_3^{2+}$, $Rh(bpy)_3^{2+}$, and other metals coordinated with bipyridines or other homolyptic compounds. Tris(2,2'-bipyridine)osmium$1^{2+}$ can be used to oxidize ferrocene, hydroquinine, catechols such as dopamine, norepinephrine and indoles such as serotonin and 5-hydroxyindole acetic acid, and ferrocene. Exemplary electron donors include, hydroxyl-containing amines, carboxyl-containing amines, such as glycine, and triethanolamine. Electron donors and acceptors are used with photosensitizers to form an electron transfer chain. Electron donors and acceptors can be capable of redox cycling, or not be capable of redox cycling, and can be replenished during a sequencing run. This replenishment can be continuous, or can be periodic.

Figure 5:
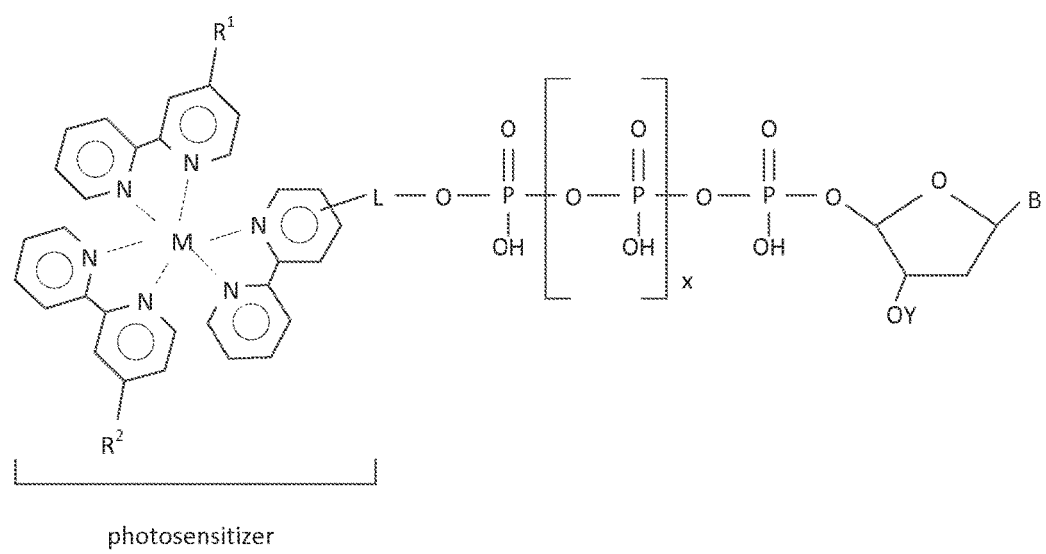
FIG. 5 illustrates a photosensitizer-labeled nucleotide.

FIG. 5 illustrates an exemplary photosensitizer-labeled nucleotide useful in embodiments of the invention. In FIG. 5, B is adenine (A), cytosine (C), guanine (G), thymine (T), uracil (U), or modified versions of any of the aforementioned nucleobases where the modifications can include terminators or virtual terminators (moieties that cause nucleic acid synthesis to stop with the incorporation of the modified nucleic acid), or can include other synthetic bases such as inosine which can pair less or more specifically than natural bases; Y is H, a terminator moiety (a moiety that causes nucleic acid synthesis to stop with the incorporation of the modified nucleic acid), or a photosensitizer label moiety, where the terminator or photosensitizer label moiety can be chemically or photochemically cleavable; L is a linker and is nothing, an alkane carbon chain, or another linker as described herein; M is $Ru^{2+}$, $Cr^{2+}$, $Fe^{2+}$, $Co^{2+}$, or $Rh^{2+}$; $R^1$ and $R^2$ are independently, H, an alkyl group, such as a methyl group, a metal ion containing complex (such as, $Ru(bpy)_3^{2+}$, derivatives of $Ru(bpy)_3^{2+}$, $Cr(bpy)_3^{2+}$, $Fe(bpy)_3^{2+}$, $Co(bpy)_3^{2+}$, or $Rh(bpy)_3^{2+}$); and x is 1 or more, and can include modifications and substitutions to the phosphate chain. The bipyridine complex can be either a Δ or a Λ isomer. In additional embodiments, modifications to the ribose can be made, which can be chemically cleavable or photo cleavable modifications or additions to the 2' position of the ribose, and can include terminators and other photosensitizer moieties. In alternate embodiments, the photosensitizer is attached to the base of the nucleic acid through a cleavable linker. Cleavable linkers are, for example, amidoallyl, nitrobenzyl groups, azidomethyl groups, and 3' O-allyl groups. After complementary nucleotide incorporation into the growing primer strand and detection of the incorporated nucleotide, the photosensitizer can be cleaved from the incorporated base by chemical cleavage, which can include palladium catalyzed allyl cleavage, tris(2-carboxyethyl) phosphine (TCEP) azido cleavage, or light cleavage of nitrobenzyl groups.

In some embodiments, uniquely identifiable labels can be comprised of multiple photosensitizers bound to a nucleotide, where one uniquely identifiable label can have more of the same photosensitizer than another different uniquely identifiable label, and the labels can be uniquely distinguished by determining differences in currents or voltages associated with the different labels. In further embodiments, multiple different types of photosensitizers can be combined as part of a single uniquely identifiable label. For example, a set of four uniquely identifiable labels can comprise: 100% label A, 66% label A and 33% label B, 33% label A and 66% label B, and 100% label B.

Figure 6A:
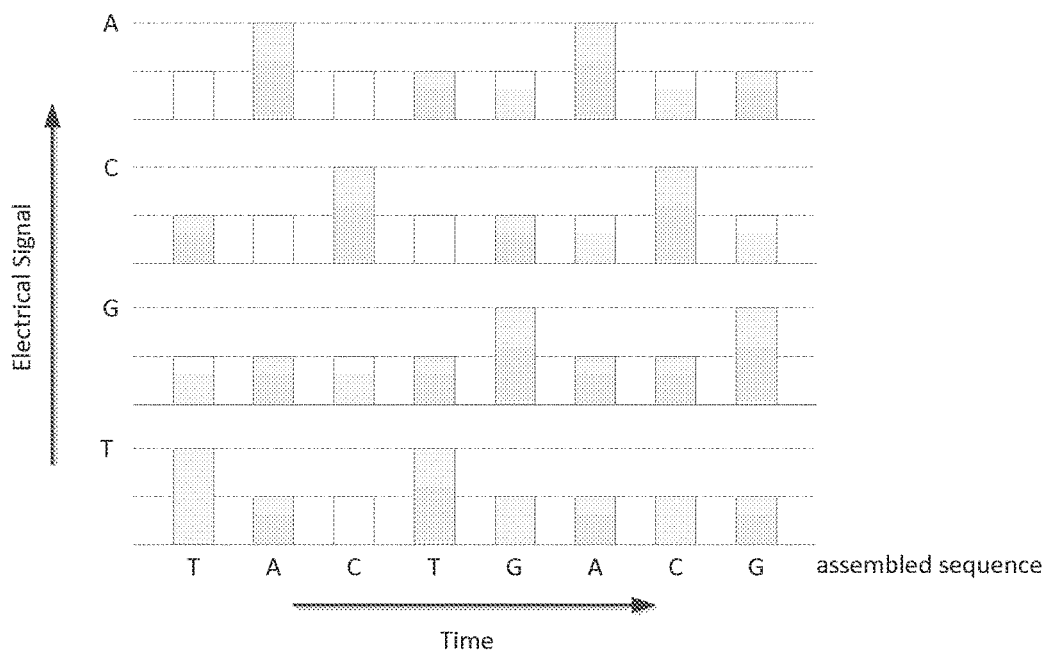
FIGS. 6A-B schematically illustrate a method for sequencing a nucleic acid molecule.

In a first embodiment, sequence data is obtained by dividing the DNA sample to be sequenced into four sub-samples or by repeating the sequencing by denaturation and removal of the second strand, followed by resequencing of the template strand using a different set of nucleotides with a different label encoding. The DNA sample can be associated with primers prior to, after, or during association with the polymerase. Each sub-sample is placed on a different array of sensors (or a different fluidically segregated (separated) region of an array of sensors) that have immobilized polymerase in the sensor region and optional sensor-associated light harvesting antennas. The first sub-sample is reacted with a reaction mixture having three types of nucleotides (e.g., A, C, G) that are labeled with a common uniquely identifiable photosensitizer label and a fourth type of nucleotide (e.g., T) labeled with a different uniquely identifiable photosensitizer label. The second sub-sample is reacted with a reaction mixture containing three types of nucleotides (e.g., A, C, T) that are labeled with a common photosensitizer label and a fourth type of nucleotide (e.g., G) labeled with a different uniquely identifiable photosensitizer label. The third and fourth sub-samples are treated similarly with the fourth type of nucleotide that is labeled being a different label from the two other sub-samples (e.g., A and C, respectively). In alternate embodiments, the fourth sub-sample is not used. The nucleotides labeled with the common photosensitizer label are used for base counting, and the nucleotide labeled with the distinct label is used for base identification. The type of data that can be obtained is illustrated schematically in FIG. 6A where only the differently labeled uniquely identifiable photosensitizer label data is depicted. The sequence of the DNA sample is assembled according to the sequence of the photosensitizer label signals from the data from the four sub-groups (labeled "A," "C," "G," and "T" in FIG. 6A). The different photosensitizer labels are detected, for example, though the intensity of the electronic signal at the sensor (e.g., number of electrons per second) generated for an amount of light input. The base encoding scheme described herein is an over determined system, which is capable of single error per frame (base) corrections.

In alternative embodiments, an encoding scheme can be used, which is not capable of either error correction or error detection within a frame (base), but requires only two sets of data for each sequence, using a simple binary encode scheme. In further embodiments, an error detection scheme can be used, where a single error within a data frame (base) can be detected, but not corrected. In yet additional embodiments, encoding schemes which permit detection of more than one error and or correction of more than one error per frame can be used.

Simple Binary Single Error Detection

| A 11 | 110 |
| G 10 | 101 |
| C 01 | 011 |
| T 00 | 000 |

Figure 6B:
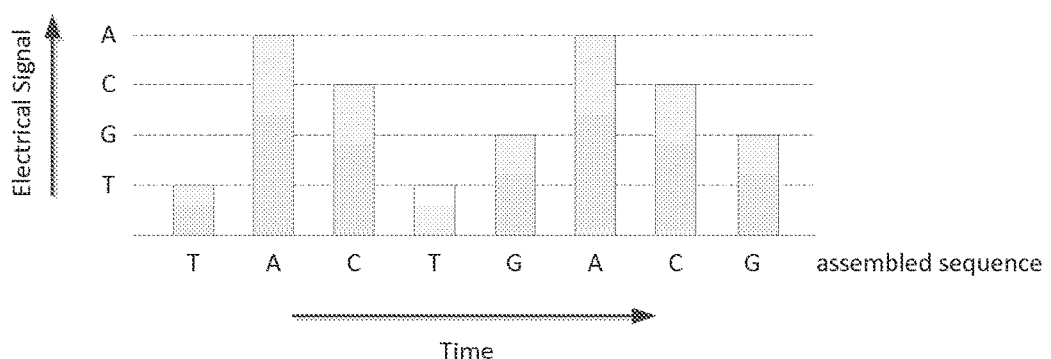

In alternate embodiments, sequence data is obtained by placing the DNA sample to be sequenced on an array of sensors that have immobilized polymerase in the sensor region and optional sensor-associated light harvesting antennas. The DNA sample can be associated with primers prior to, after, or during association with the polymerase. The DNA sample on the sensor array is reacted with a reaction mixture containing photosensitizer-labeled nucleotides in which each different nucleotide (A, C, T, and G) is labeled with a different uniquely identifiable photosensitizer label. The type of data that can be obtained is illustrated schematically in FIG. 6B. The different photosensitizer labels are detected, for example, though the intensity of the electronic signal (e.g., number of electrons per second) generated for an amount of light input or can be detected as currents through different working electrodes associated with different electron transfer chains associated with the different uniquely identifiable photosensitizer labels, or can be detected by a combination of different current levels on a working electrode combined with currents being associated with different working electrodes. The different signals over time from labeled nucleotides are indicated as "A," "C," "G," and "T" in FIG. 6B.

In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, mitochondrial DNA, a gene or a portion thereof, a cDNA, RNAs involved in protein synthesis such as mRNA, RNAs involved in post transcriptional modifications such as snRNA, regulatory RNAs such as miRNA, parasitic RNAs such as viral RNAs, a synthetic nucleic acid sequence, or a combination of one or more synthetic and one or more natural nucleic acid sequences, which can include nucleic acid barcodes used for sample identification and or portions of primers which can be used so as to provide a known initial sequence and can be used to normalize signal levels for individual sensors. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides. Analogs and synthetic nucleotides are molecules that have structural features in common with natural nucleotides such that when incorporated into a nucleic acid or when forming a nucleic acid molecule they allow hybridization with a complementary polynucleotide in solution. Analogs can have substitutions in or additions to the phosphate groups, the base, the sugar group, or a combination thereof of a nucleotide.

In some embodiments, a synchronous chemistry is used, such as a sequencing chemistry that uses nucleotides with terminators or multiple flows which include less than all four nucleotides. In other embodiments, an asynchronous chemistry can be used, in which all four nucleobases can be provided without terminators, allowing a continuous sequencing chemistry. In some embodiments it can be desirable to use four different uniquely identifiable labels, such that one uniquely identifiable label can be associated with each nucleobase. The system can be configured to have more than one working electrode associated with each sensor region, where different working electrodes of the working electrodes associated with each sensor region can be configured to operate at different working potentials; the different working electrodes associated with each sensor region can be used with different electron transfer chains, where the different electron transfer chains can use different photosensitizers, and where the different photosensitizers can use a single input light source for activation, or can used different lights sources with different wavelengths for activation.

In some embodiments, light sources can be illuminated simultaneously for systems in which the electron transfer chains can be uniquely associated with the different uniquely identifiable labels, and thus with four different working electrodes. This can be particularly desirable for asynchronous chemistries in which it can be desirable to simultaneously monitor for all uniquely identifiable labels. In alternative embodiments, the light sources can alternate, allowing identification of uniquely identifiable labels by determination of the wavelength of light required for photo activation of the photosensitizer, permitting the use of fewer working electrodes, as some working electrodes can be used for more than one uniquely identifiable label. In some embodiments the light sources can be applied in a sequential manner, such that no two light sources are illuminating the photosensitizers at the same time. In other embodiments, other sequential patterns can be used, wherein more than one light source at a time can be illuminated, which can allow for as few as a single working electrode being associated with each sensor region, particularly for systems wherein the wavelengths of light associated with the two or more simultaneously applied wavelengths of light can interact with electron chains which can be identified by different working electrodes.

In some embodiments, fewer than four uniquely identifiable labels can be used, particularly for a system which is used in a synchronous manner as described herein, where a label coding system can be used to determine which base is incorporated, where multiple sequence reactions can be performed of the same portion of the same strand in the same sensor region. The template strand of nucleic acid can be bound to the polymerase, to an end of an antenna that interacts with the sensor region, or to a structure within the sensor region. In some embodiments, specific or universal primers can be provided so as to generate double stranded DNA where the polymerase can be used with photosensitizer-labeled nucleotides to perform a sequencing reaction. In other embodiments, a hairpin primer can be used as a part of the template strand. A sequencing reaction can be performed to the length desired, which can be of the full length of the template strand, or can be for a portion of the template strand, after which the strand complementary to the template strand can be denatured and removed. The denaturation can be a heat denaturation, or can be a chemical denaturation. For embodiments which use a hairpin primer, a restriction site, which can be a restriction site not normally found in the genome being sequenced, can be cleaved with an appropriate restriction enzyme prior to denaturation.

A variety of polymerases are available that can incorporate ribonucleotides or modified nucleotides into nucleic acids, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research,* 31:14, 4129-4137 (2003); and Gao, G., Orlova, M., Georgiadis, M. M., Hendrickson, W. A., Goff, S. P., *Proceedings of the National Academy of Sciences,* 94, 407-411 (1997).

Dielectric materials also include, for example, $SiO_2$, SiN, and SiON, among others.

Persons skilled in the relevant art appreciate that modifications and variations are possible throughout the disclosure as are substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Various additional layers and or structures can be included and or described features can be omitted in other embodiments.

What is claimed is:

1. A system comprising:
 a substrate, having a surface, which comprises an intergrated circuit;
 an enzyme to couple to the substrate and to a DNA molecule;
 a photosensitizer to couple to a nucleotide and to the enzyme;
 sensors, individually addressable through the intergrated circuit, which are on the substrate surface and include a first sensor to couple to the enzyme; and
 antennas on the substrate surface, adjacent the first sensor, and oriented to localize light towards the first sensor;
 wherein the photosensitizer is configured to communicate electrons between the photosensitizer and at least one of an electron receptor or an electron donor in response to: (a) the photosensitizer and the DNA molecule both coupling to the enzyme, and (b) the photosensitizer being exposed to localized light from the antennas;
 wherein the first sensor is configured to sense the electrons communicated with the photosensitizer to indicate the nucleotide is coupled to the DNA molecule.

2. The system of claim 1, wherein a layer covers a first portion of the first sensor, but not a second portion of the first sensor, and the layer includes a dielectric.

3. The system of claim 2, wherein (a) a first antenna of the antennas is bigger than a second antenna of the antennas, and (b) the first antenna is configured to harvest light of a first wavelength and the second antenna is configured to harvest light of a second wavelength unequal to the first wavelength.

4. The system of claim 3, wherein the first antenna harvests light for both the first sensor and a second sensor included in the sensors.

5. The system of claim 4, wherein the first sensor includes a surface comprising the electron acceptor and the electron acceptor includes a derivative of bipyridium.

6. The system of claim 4, wherein the first sensor includes a surface comprising the electron acceptor.

7. The system of claim 1 wherein (a) a first antenna of the antennas is bigger than a second antenna of the antennas, and (b) the first antenna is configured to harvest light of a first wavelength and the second antenna is configured to harvest light of a second wavelength unequal to the first wavelength.

8. The system of claim 1, wherein the first sensor includes a surface comprising the electron acceptor and the electron acceptor includes a derivative of bipyridium.

9. The system of claim 1, wherein the first sensor includes a surface comprising the electron acceptor.

10. The system of claim 1, wherein a first antenna of the antennas harvests light for both the first sensor and a second sensor included in the sensors.

11. The system of claim 10, wherein:
a layer covers a first portion of a surface of the first sensor but not a second portion of the surface of the first sensor;
the layer includes a dielectric;
the first sensor is between the surface of the first sensor and the substrate;
the substrate includes a long axis that defines its width;
the surface is generally parallel to the long axis.

12. The system of claim 10, wherein:
a layer covers a first portion of a top surface of the first sensor but not a second portion of the top surface;
the top surface directly connects to a side surface of the first sensor;
the side surface is between the top surface and a bottom surface of the first sensor; and
the bottom surface is between the top surface and a bottom surface of the substrate.

13. A system comprising:
a substrate, having a surface, which comprises an integrated circuit;
an enzyme to couple to the substrate and to a DNA molecule;
a photosensitizer to couple to a nucleotide and to the enzyme;
sensors, individually addressable through the integrated circuit, which are on the substrate surface and include a first sensor to couple to the enzyme; and
antennas on the substrate surface, adjacent the first sensor, and oriented to localize light towards the first sensor;
wherein (a) a first antenna of the antennas is bigger than a second antenna of the antennas, and (b) the first antenna is configured to harvest light of a first wavelength and the second antenna is configured to harvest light of a second wavelength unequal to the first wavelength.

14. The system of claim 13 wherein the first antenna harvests light for both the first sensor and a second sensor included in the sensors.

15. The system of claim 13 wherein:
a layer covers a first portion of a surface of the first sensor but not a second portion of the surface of the first sensor;
the layer includes a dielectric;
the first sensor is between the surface of the first sensor and the substrate;
the substrate includes a long axis that defines its width;
the surface is generally parallel to the long axis.

16. The system of claim 15 wherein:
the photosensitizer is to communicate electrons between the photosensitizer and at least one of an electron receptor or an electron donor in response to: (a) the photosensitizer and the DNA molecule both coupling to the enzyme, and (b) the photosensitizer being exposed to localized light from the antennas;
the first sensor is to sense the electrons communicated with the photosensitizer to indicate the nucleotide is coupled to the DNA molecule.

17. A system comprising:
a substrate, having a surface, which comprises an integrated circuit;
sensors, individually addressable through the integrated circuit, which are on the substrate surface and include a first sensor configured to couple to an enzyme; and
antennas on the substrate surface, adjacent the first sensor, and oriented to localize light towards the first sensor;
wherein (a)(i) a first antenna of the antennas is bigger than a second antenna of the antennas, and (a)(ii) the first antenna is configured to harvest light of a first wavelength and the second antenna is configured to harvest light of a second wavelength unequal to the first wavelength;
wherein the first antenna harvests light for both the first sensor and a second sensor included in the sensors;
wherein: (b)(i) a layer covers a first portion of a surface of the first sensor but not a second portion of the surface of the first sensor; (b)(ii) the layer includes a dielectric; (b)(iii) the first sensor is between the surface of the first sensor and the substrate; (b)(iv) the substrate includes a long axis that defines its width; and (b)(v) the surface is generally parallel to the long axis.

18. The system of claim 17 comprising at least one of the enzyme or a photosensitizer, wherein:
the photosensitizer is to communicate electrons between the photosensitizer and at least one of an electron receptor or an electron donor in response to: (a) the photosensitizer and a DNA molecule both coupling to the enzyme, and (b) the photosensitizer being exposed to localized light from the antennas;
the first sensor is to sense the electrons communicated with the photosensitizer to indicate a nucleotide is coupled to the DNA molecule.

* * * * *